United States Patent
Morita et al.

(10) Patent No.: US 6,280,748 B1
(45) Date of Patent: *Aug. 28, 2001

(54) COSMETIC RAW MATERIAL COSMETIC PRODUCT AND METHOD FOR MANUFACTURING COSMETIC PRODUCTS

(75) Inventors: Yoshitsugu Morita; Haruhiko Furukawa; Takayuki Aso; Tadashi Hamachi, all of Chiba Prefecture (JP)

(73) Assignee: Dow Corning Toray Silicone, Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/318,997

(22) Filed: May 26, 1999

(30) Foreign Application Priority Data

Jun. 12, 1998 (JP) .................................................. 10-181649

(51) Int. Cl.⁷ ...................................................... A61K 7/00
(52) U.S. Cl. ...................... 424/401; 424/70.1; 424/70.11; 424/70.12; 424/70.121; 424/70.122; 514/772.1; 514/772.2; 514/772.3
(58) Field of Search ................................... 424/401, 70.1, 424/70.11, 70.12, 70.121, 70.122; 514/772.1, 772.2, 772.3

(56) References Cited

U.S. PATENT DOCUMENTS

| 4,665,145 | * | 5/1987 | Yokota et al. | 526/279 |
| 5,929,187 | * | 7/1999 | Yoshitake | 528/15 |

FOREIGN PATENT DOCUMENTS

| 1 055 674 A1 | * | 11/2000 | (EP) . |
| 5-924 | | 1/1993 | (JP) . |
| 5-213722 | * | 8/1993 | (JP) . |
| 9-59132 | | 3/1997 | (JP) . |
| 9-208422 | | 8/1997 | (JP) . |
| 11-1530 | | 1/1999 | (JP) . |
| 95/23889 | * | 9/1995 | (WO) . |

* cited by examiner

Primary Examiner—Jose' G. Dees
Assistant Examiner—Frank Choi
(74) Attorney, Agent, or Firm—James L. De Cesare

(57) ABSTRACT

A cosmetic raw material possesses excellent compounding stability in cosmetic products. The cosmetic raw material is produced from a vinyl-type polymer having a carbosiloxane dendrimer structure in its side molecular chain. The cosmetic raw material is composed of the vinyl-type polymer having a carbosiloxane dendrimer structure in its side molecular chain, and a solution or a dispersion of a liquid such as a silicone oil, organic oil, alcohol, or water.

2 Claims, No Drawings

COSMETIC RAW MATERIAL COSMETIC PRODUCT AND METHOD FOR MANUFACTURING COSMETIC PRODUCTS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

The present invention relates to cosmetic raw materials, in particular to cosmetic raw materials which impart excellent compounding stability, a pleasant sense of use, and surface protection properties to cosmetic products. The invention also relates to cosmetic products, and to a method of manufacturing the cosmetic products.

BACKGROUND OF THE INVENTION

It is known to use a copolymer of an organopolysiloxane and a radical-polymerizable monomer as a cosmetic raw material. For example, Japanese Laid-Open Patent Application Kokai No. 5-924 suggests using a vinyl polymer obtained by polymerizing a dimethylpolysiloxane oligomer that contains methacrylic groups with tertiary butyl acrylate and methacrylic acid as a base oil for a hair conditioner. Japanese Laid-Open Patent Application Kokai No. 9-59132 discloses a hair cosmetic material which contains an alternating block copolymer of a polydimethylsiloxane and a polyoxyalkylene. Furthermore, Japanese Laid-Open Patent Application Kokai No. 9-208,422 discloses a cosmetic composition which contains an emulsion obtained by polymerizing an organopolysiloxane with butyl acrylate, methacrylic acid, styrene, and acrylic acid. However, these cosmetic raw materials have poor affinity to other cosmetic raw materials and show unsatisfactory compounding stability with respect to cosmetic products. While these cosmetic raw materials impart hydrophobic properties and smoothness to cosmetic products, they impair adhesion to hair and skin, can be easily removed from hair and skin, and impair surface-protective properties.

BRIEF SUMMARY OF THE INVENTION

It is an object of the present invention to provide a cosmetic raw material which imparts excellent compounding stability, a pleasant sense of use, and surface-protective properties to cosmetic products. It is another object to provide cosmetic products and a method for the preparation of cosmetic products.

DETAILED DESCRIPTION OF THE INVENTION

The present invention relates to a cosmetic raw material which is composed of a vinyl polymer having a carbosiloxane dendrimer structure in its side molecular chain. The invention also relates to a cosmetic raw material composed of the vinyl-type polymer and a solution or a dispersion of a liquid such as a silicone oil, organic oil, alcohol, and water. The invention also relates to cosmetic products prepared from the cosmetic raw material in combination with other cosmetic raw materials, as well as to a method for their preparation.

The cosmetic raw material of the present invention is characterized by a vinyl-type polymer which has in its side molecular chain a carbosiloxane dendrimer structure. The term "carbosiloxane dendrimer structure" in the context of the present invention is a structure with high-molecular-weight groups branched with high regularity in a radial direction from a single core. Such carbosiloxane dendrimer structures are described in the form of a highly-branched siloxane-silalkylene copolymer in Japanese Laid-Open Patent Application Hei 11-1530.

In the cosmetic raw material of the present invention, the carbosiloxane dendrimer structure of a vinyl-type polymer can be represented by the following general formula:

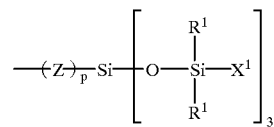

where Z is a divalent organic group such as an alkylene group, an arylene group, an aralkylene group, an ester-containing divalent organic group, an ether-containing divalent organic group, a ketone-containing divalent organic group, or an amide-containing divalent organic group. Preferable organic groups are represented by the following formulae:

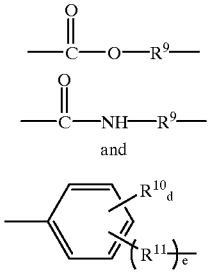

and where $R^9$ is an alkylene group with 1 to 10 carbon atoms such as a methylene group, ethylene group, propylene group, or butylene group, with the methylene group and propylene group being preferable; $R^{10}$ is represented by an alkyl group having 1 to 10 carbon atoms, such as a methyl group, an ethyl group, a propyl group, or a butyl group, with the methyl group being preferable; $R^{11}$ is represented by an alkylene group having 1 to 10 carbon atoms, such as a methylene group, an ethylene group, a propylene group, a butylene group, with the ethylene group being preferable; d is an integer between 0 and 4; and e is 0 or 1. $R^1$ is an alkyl group or an aryl group with 1 to 10 carbon atoms where the alkyl group is represented by a methyl group, an ethyl group, a propyl group, a butyl group, a pentyl group, an isopropyl group, an isobutyl group, a cyclopentyl group, or a cyclohexyl group; the aryl group is represented by a phenyl group and a naphthyl group. The methyl and phenyl group are preferable, but the methyl group is most preferable. $X^1$ represents a silylalkyl group expressed by the following formula when i is equal to one:

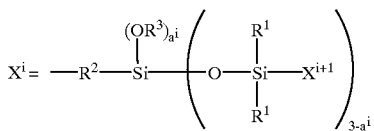

In this formula, $R^1$ is the same as defined above, $R^2$ is an alkylene group having 2 to 10 carbon atoms such as an ethylene group, a propylene group, a butylene group, a hexylene group, or a similar linear alkylene group; a methylmethylene group, a methylethylene group, 1-methylpentylene group, 1,4-dimethylbutylene group or a similar branched alkylene group. The ethylene group, methylethylene group, hexylene group, 1-methylpentylene group, and 1,4-dimethylbutylene group are preferable. $R^3$ is an alkyl group having 1 to 10 carbon atoms, such as a methyl group, an ethyl group, a propyl group, a butyl group, and an isopropyl group. In the above formula, i is an integer between 1 and 10 that shows the generation of the silylalkyl group; and $a^i$ is an integer from 0 to 3.

The following vinyl-type polymer which contains a carbosiloxane dendrimer structure is preferable for the cosmetic raw material of the present invention:

(A) 0 to 99.9 parts by weight of a vinyl-type monomer; and (B) 100 to 0.1 parts by weight of a carbosiloxane dendrimer which contains a radical-polymerizable organic group represented by the following general formula:

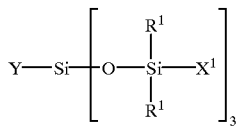

where Y is a radical-polymerizable organic group, $R^1$ is an aryl group or an alkyl group having 1 to 10 carbon atoms, wherein the alkyl group is represented by a methyl group, an ethyl group, a propyl group, a butyl group, a pentyl group, an isopropyl group, an isobutyl group, a cyclopentyl group, a cyclohexyl group, and where the aryl group is represented by a phenyl group and a naphthyl group, where the methyl and phenyl group are preferable and the methyl group is most preferable; and $X^1$ is a silylalkyl group which, when i=1, is expressed by the following formula:

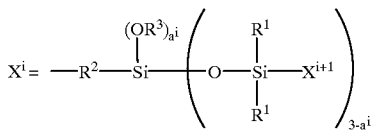

where $R^1$ is the same as defined above, $R^2$ is an alkylene group with 2 to 10 carbon atoms $R^3$ is an alkyl group having 1 to 10 carbon atoms; $X^{i+1}$ is a hydrogen atom, an alkyl group having 1 to 10 carbon atoms, an aryl group, or the silylalkyl group; i is an integer from 1 to 10 which shows the generation of the silylalkyl group, and $a^i$ is an integer from 0 to 3.

The vinyl-type monomer which is component (A) in the vinyl-type polymer of the present invention is a vinyl-type monomer which contains a radical polymerizable vinyl group. There are no particular limitations with regard to the type of such a monomer. The following are examples of this vinyl-type monomer: methyl methacrylate, ethyl methacrylate, n-propyl methacrylate, isopropyl methacrylate, or similar lower alkyl methacrylate; glycidyl methacrylate; n-butyl methacrylate, isobutyl methacrylate, tert-butyl methacrylate, n-hexyl methacrylate, methacrylic acid, cyclohexyl-2-ethylhexyl methacrylate, octyl methacrylate, lauryl methacrylate, stearyl methacrylate, or similar higher methacrylate; vinyl acetate, vinyl propionate, or similar lower fatty acid vinyl ester; vinyl caproate, vinyl-2-ethylhexoate, vinyl laurate, vinyl stearate, or similar higher fatty acid ester; styrene, vinyl toluene, benzyl methacrylate, phenoxyethyl methacrylate, vinyl pyrrolidone, or similar aromatic vinyl monomers; methacrylamide, N-methylol methacrylamide, N-methoxymethyl methacrylamide, isobutoxymethoxy methacrylamide, N,N-dimethyl methacrylamide, or similar vinyl-type monomers which contain amide groups; hydroxyethyl methacrylate, hydroxypropyl alcohol methacrylate, or similar vinyl-type monomers which contain hydroxyl groups; methacylic acid, itaconic acid, crotonic acid, fumaric acid, maleic acid, or similar vinyl-type monomers which contain a carboxylic acid group; tetrahydrofurfuryl methacrylate, butoxyethyl methacrylate, ethoxy diethylene glycol methacrylate, polyethylene glycol methacrylate, polypropylene glycol monomethacrylate, hydroxybutyl vinyl ether, cetyl vinyl ether, 2-ethylhexyl vinyl ether, or similar ether-bonded vinyl-type monomer; methacryloxypropyl trimethoxysilane, polydimethylsiloxane having a methacrylic group on one of its molecular terminals, polydimethylsiloxane having a styryl group on one of its molecular terminals, or similar silicone compound having unsaturated groups; butadiene; vinyl chloride; vinylidene chloride; methacrylonitrile; dibutylfumarate; anhydrous maleic acid; anhydrous succinic acid; methacrylglycidyl ether; an organic amine salt, an ammonium salt, and an alkali metal salt of methacrylic acid, itaconic acid, crotonic acid, maleic acid, or fumaric acid; a radical-polymerizable unsaturated monomer having a sulfonic acid group such as a styrene sulfonic acid group; a quaternary ammonium salt derived from a methacrylic acid such as 2-hydroxy-3-methacryloxypropyl trimethylammonium chloride; and a methacrylic acid ester of an alcohol having a tertiary amine group such as a methacrylic acid diethylamine ester; and an above-mentioned vinyl-type monomers of which methacrylate is replaced by acrylates, methacrylic amide is replaced by acrylic amide and methacrylic acid is replaced by acrylic acid.

Multifunctional vinyl-type monomers can also be used for the purposes of the invention. The following are examples of such compounds: trimethylolpropane trimethacrylate, pentaerythritol trimethacrylate, ethylene glycol dimethacrylate, tetraethylene glycol dimethacrylate, polyethylene glycol dimethacrylate, 1,4-butanediol dimethacrylate, 1,6-hexanediol dimethacrylate, neopentyl glycol dimethacrylate, trimethylolpropane trioxyethyl methacrylate, tris-(2-hydroxyethyl) isocyanurate dimethacrylate, tris-(2-hydroxyethyl) isocyanurate trimethacrylate, polydimethylsiloxane capped with styryl groups having divinylbenzene groups on both terminals, or similar silicone compounds having unsaturated groups; and an above-mentioned multifunctional vinyl-type monomers of which methacrylate is replaced by acrylates.

Carbosiloxane dendrimer which is component (B) is represented by the following general formula:

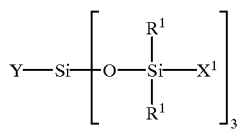

where Y is a radical-polymerizable organic group or an organic group which is suitable for radical reactions. The following are specific examples of such groups: organic groups which contain methacrylamide groups, organic groups which contain styryl groups or alkenyl groups having 2 to 10 carbon atoms, and organic groups which contain methacryloxy groups, shown by the formulae given below:

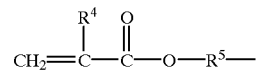

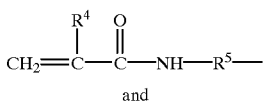

and

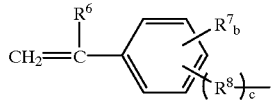

where $R^4$ and $R^6$ are hydrogen atoms or methyl groups, $R^5$ and $R^8$ are alkylene groups having 1 to 10 carbon atoms, $R^7$ is an alkyl group having 1 to 10 carbon atoms; b is an integer from 0 to 4, and c is 0 or 1. The following are examples of the radical-polymerizable organic groups: an acryloxymethyl group, 3-acryloxypropyl group, a methacryloxymethyl group, a 3-methacryloxypropyl group, a 4-vinylphenyl group, a 3-vinylphenyl group, a 4-(2-propenyl) phenyl group, a 3-(2-propenyl) phenyl group, a 2-(4-vinylphenyl) ethyl group, a 2-(3-vinylphenyl) ethyl group, a vinyl group, an allyl group, a methallyl group, and a 5-hexenyl group. $R^1$ is an alkyl group or an aryl group having 1 to 10 carbon atoms, where the alkyl group can be a methyl group, an ethyl group, a propyl group, a butyl group, a pentyl group, an isopropyl group, an isobutyl group, a cyclopentyl group, or a cyclohexyl group; and the aryl group can be a phenyl group or a naphthyl group. Most preferable are the methyl and phenyl group, with the methyl group most preferable. $X^1$ is a silylalkyl group which is represented by the following formula when i is equal to one:

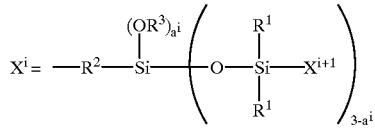

where $R^2$ is an alkylene group having 2 to 10 carbon atoms, such as an ethylene group, a propylene group, a butylene group, a hexylene group, or similar linear alkylene group; a methylmethylene group, a methylethylene group, a 1-methylpentylene group, a 1,4-dimethylbutylene group, or a similar branched alkylene group. The most preferable are ethylene, methylethylene, hexylene, 1-methylpentylene and 1,4-dimethylbutylene. $R^3$ represents an alkyl group having 1 to 10 carbon atoms, such as methyl, ethyl, propyl, butyl, and isopropyl groups. $R^1$ is the same as defined above. $X^{i+1}$ is a hydrogen atom, an alkyl group having 1 to 10 carbon atoms, an aryl group, or the silylalkyl group. $a^i$ is an integer from 0 to 3, and i is an integer from 1 to 10 shows the generation count which is the number of repetitions of the silylalkyl group. For example, when the generation count is one, the carbosiloxane dendrimer can be expressed by the first general formula shown below, where Y, $R^1$, $R^2$ and $R^3$ are the same as defined above, $R^{12}$ is a hydrogen atom or the same as $R^1$; $a^1$ is the same as $a^i$ but the total average number of $a^1$ in one molecule is within a range of 0 to 7. When the generation count is 2, the carbosiloxane dendrimer can be expressed by the second general formula shown below, where Y, $R^1$, $R^2$, $R^3$ and $R^{12}$ are the same as defined above; $a^1$ and $a^2$ are the same as $a^i$, but the total average number of $a^1$ and $a^2$ in one molecule is within a range of 0 to 25. In the case where the generation count is 3, the carbosiloxane dendrimer is represented by the third general formula shown below, where Y, $R^1$, $R^2$, $R^3$ and $R^{12}$ are the same as defined above; $a^1$, $a^2$ and $a^3$ are the same as $a^i$, but the total average number of $a^1$, $a^2$ and $a^3$ in one molecule is within a range of 0 to 79.

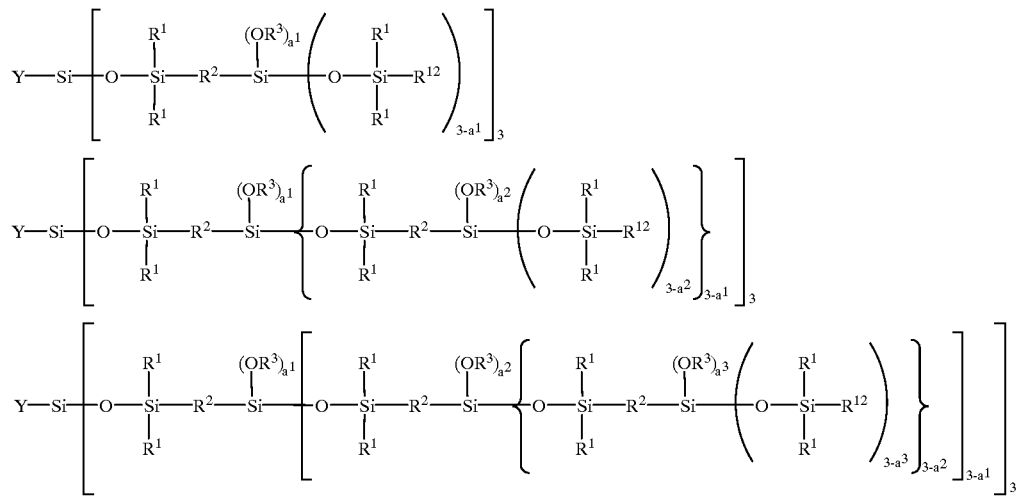

A carbosiloxane dendrimer of the present invention which contains a radical-polymerizable organic group can be represented by the following average structural formulae:
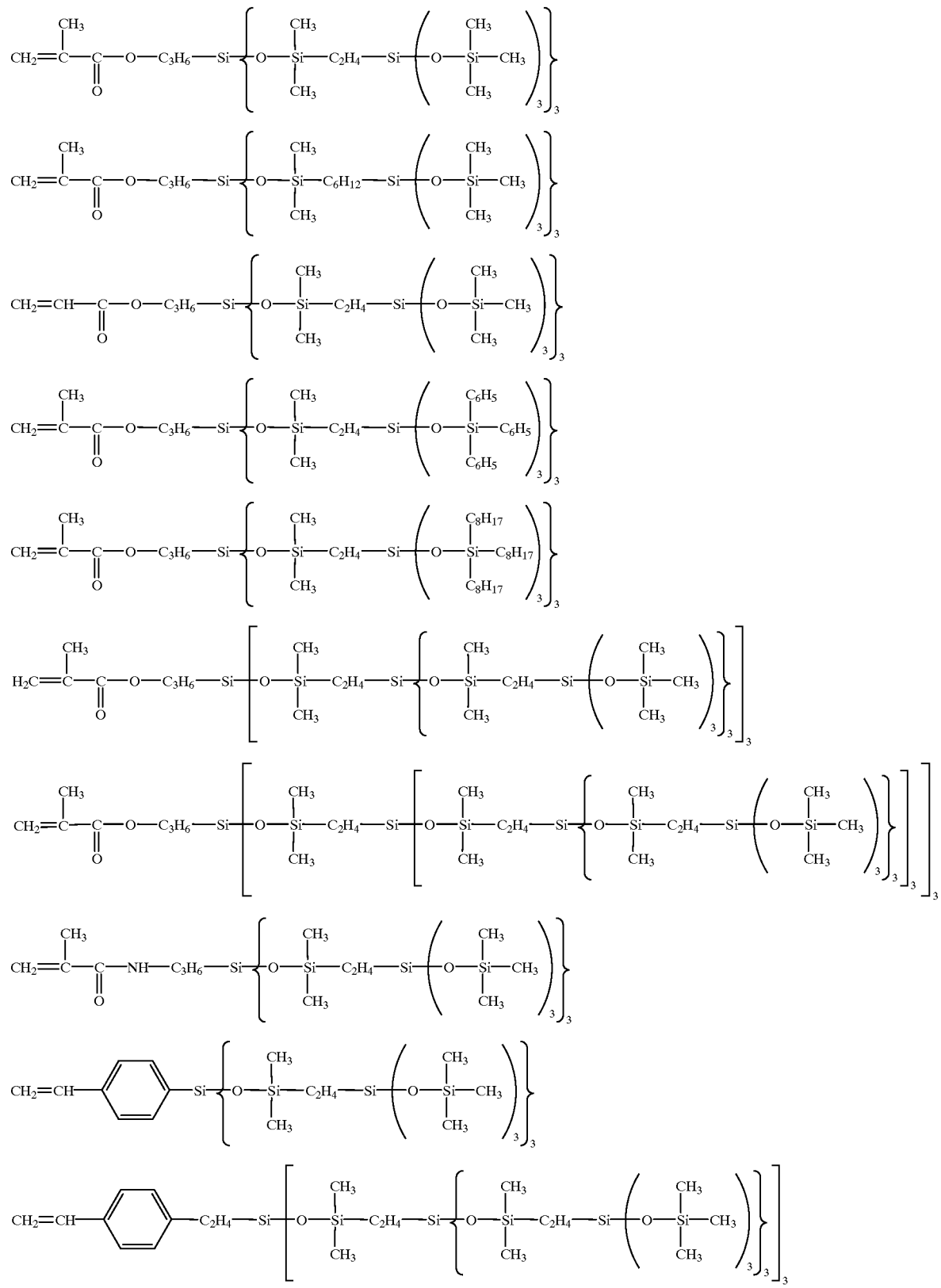

-continued

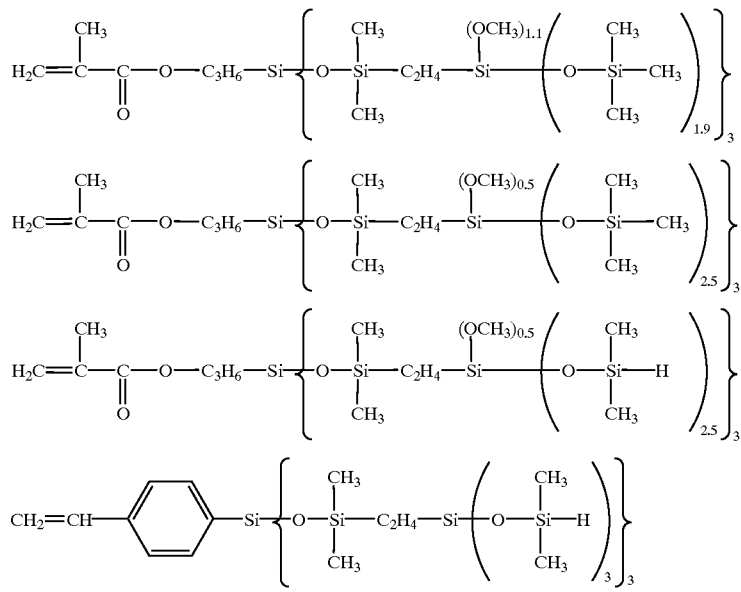

The carbosiloxane dendrimer can be manufactured in accordance with the procedure for manufacturing a branched siloxane-silalkylene disclosed in Japanese Patent Application Hei 11-1530. For example, it can be produced by subjecting to a hydrosilylation reaction an organosilicon compound which contains a silicon-bonded hydrogen atom represented by the following general formula:

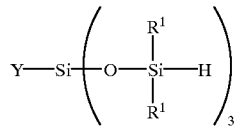

and an organosilicon compound which contains an alkenyl group. In the above formula, the organosilicon compound can be represented by 3-methacryloxypropyl tris-(dimethylsiloxy) silane, 3-acryloxypropyl tris-(dimethylsiloxy) silane, and 4-vinylphenyl tris (dimethylsiloxy) silane. The organosilicon compound which contains an alkenyl group can be represented by vinyl tris-(trimethylsiloxy) silane, vinyl tris-(dimethylphenylsiloxy) silane, and 5-hexenyl tris-(trimethylsilyloxy) silane. The hydrosilylation reaction is conducted in the presence of a chloroplatinic acid, a platinum vinylsiloxane complex, or similar transition metal catalyst.

It is preferred that in the vinyl-type polymer of the present invention which contains a dendrimer structure, the polymerization ratio of components (A) and (B), in terms of the weight ratio of (A) to (B), be within a range of 0:100 to 99.9:0.1, and preferably within a range of 1:99 to 99:1. A ratio of (A) to (B) components of 0:100 means that the compound becomes a homopolymer of component, (B).

The vinyl-type polymer contains a carbosiloxane dendrimer structure and this polymer may be obtained either by copolymerizing components (A) and (B), or by polymerizing component (B) alone. Polymerization can be radical polymerization or ion polymerization, however radical polymerization is preferable. The polymerization can be performed by causing a reaction between components (A) and (B) in a solution for 3 to 20 hours in the presence of a radical initiator at a temperature of 50° C. to 150° C. A solvent suitable for this purpose is hexane, octane, decane, cyclohexane, or similar aliphatic hydrocarbon; benzene, toluene, xylene, or similar aromatic hydrocarbon; diethyl ether, dibutyl ether, tetrahydrofuran, dioxane, or similar ethers; acetone, methylethyl ketone, methylisobutyl ketone, di-isobutyl ketone, or similar ketones; methyl acetate, ethyl acetate, butyl acetate, isobutyl acetate, or similar esters; methanol, ethanol, isopropyl alcohol, butanol, or similar alcohols; octamethylcyclotetrasiloxane, decamethylcyclopentasiloxane, hexamethyldisiloxane, octamethyltrisiloxane, or similar organosiloxane oligomer. A radical initiator may be any compound known in the art for conventional radical-polymerization reactions. Specific examples of such radical initiators are 2,2'-azobis (isobutyronitrile), 2,2'-azobis (2-methylbutyronitrile), 2,2'-azobis (2,4-dimethylvaleronitrile) or similar azobis compounds; benzoyl peroxide, lauroyl peroxide, tert-butyl peroxy benzoate, tert-butyl peroxy-2-ethyl hexanoate, or similar organic peroxide. These radical initiators can be used individually or in a combination of two or more. It is preferred that the radical initiators be used in an amount of 0.1 to 5 parts by weight per 100 parts by weight of the components (A) and (B). A chain transfer agent can be added. The chain transfer agent can be 2-mercapto ethanol, butyl mercaptan, n-dodecyl mercaptan, 3-mercaptopropyl trimethoxysilane, a polydimethylsiloxane having a mercaptopropyl group or similar mercapto compound; methylene chloride, chloroform, carbon tetrachloride, butyl bromide, 3-chloropropyl trimethoxysilane, or similar halogenated compound. In the manufacture of the vinyl-type polymer of the present invention, it is preferred that after polymerization, the residual non-reacted vinyl monomer be removed by heating under vacuum conditions.

To facilitate compounding of the cosmetic raw material, it is preferred that the number-average molecular weight of the vinyl polymer which contains a carbosiloxane dendrimer, be selected within the range of 3,000 to 2,000,000, preferably between 5,000 and 800,000. It may have a liquid, gum, paste, solid, powder, or other form. Preferable forms are solutions formed by diluting in solvents, a dispersion, or a powder.

In accordance with another embodiment of the invention, the cosmetic raw material of the invention may be a dispersion of a vinyl-type polymer having a carbosiloxane dendrimer structure in its side molecular chain, in a liquid such as a silicone oil, an organic oil, an alcohol, or water.

The vinyl-type polymer having a carbosiloxane dendrimer structure in its side molecular chain, in this embodiment is the same as the one described above. The liquid may be a silicone oil, an organic oil, an alcohol, or water. The silicone oil may be a dimethylpolysiloxane having both molecular terminals capped with trimethylsiloxy groups, a copolymer of methylphenylsiloxane and dimethylsiloxane having both molecular terminals capped with trimethylsiloxy groups, a copolymer of methyl-3,3,3-trifluoropropylsiloxane and dimethylsiloxane having both molecular terminals capped with trimethylsiloxy groups, or similar linear non-reactive silicone oils, as well as hexamethylcyclotrisiloxane, octamethylcyclotetrasiloxane, decamethylcyclopentasiloxane, dodecamethylcyclohexasiloxane, or a similar cyclic compound. In addition to non-reactive silicone oils, modified polysiloxanes having functional groups such as silanol groups, amino groups, and polyether groups on the terminals or in the side molecular chains can be employed.

The organic oils can be liquid paraffin, isoparaffin, hexyl laurate, isopropyl myristate, myristil myristate, cetyl myristate, 2-octyl dodecyl myristate; isopropyl palmitate, 2-ethylhexyl palmitate, butyl stearate, decyl oleate, 2-octyldodecyl oleate, myristil lactate, cetyl lactate, lanolin acetate, stearic alcohol, cetostearic alcohol, oleic alcohol, avocado oil, almond oil, olive oil, cacao oil, jojoba oil, gum oil, sunflower oil, soybean oil, camellia oil, squalane, castor oil, mink oil, cotton seed oil, coconut oil, egg yolk oil, beef tallow, lard, polypropylene glycol monooleate, neopentyl glycol 2-ethylhexanoate, or similar glycol ester oil; triglyceryl isostearate, coconut oil fatty acid triglyceride, or similar polyhydric alcohol ester oil; polyoxyethylene lauryl ether, polyoxypropylene cetyl ether, or similar polyoxyalkylene ether.

The alcohol can be of any type suitable for use in conjunction with a cosmetic raw material. For example, it can be methanol, ethanol, butanol, isopropanol or similar lower alcohols. A solution or dispersion of the alcohol should have a viscosity within the range of 10 to $10^9$ mPa at 25° C. For improving sense of use properties in a cosmetic product, the viscosity should be within the range of 100 to $5 \times 10^8$ mPa·s.

The solutions and dispersions can be easily prepared by mixing the vinyl-type polymer having a carbosiloxane dendrimer structure, with a silicone oil, an organic oil, an alcohol, or water. The liquids can be present in the stage of polymerization of the vinyl-type polymer having a carbosiloxane dendrimer structure. In that case, the residual unreacted vinyl monomer should be completely removed by heat-treating the solution or dispersion under normal or reduced pressure. In the case of a dispersion, dispersity of the vinyl-type polymer can be improved by adding a surface-active agent. Such an agent can be hexylbenzene sulfonic acid, octylbenzene sulfonic acid, decylbenzene sulfonic acid, dodecylbenzene sulfonic acid, cetylbenzene sulfonic acid, myristilbenzene sulfonic acid, or anionic surfactants of sodium salts of these acids; octyltrimethyl ammonium hydroxide, dodecyltrimethyl ammonium hydroxide, hexadecyltrimethyl ammonium hydroxide, octyl dimethylbenzyl ammonium hydroxide, decyl dimethylbenzyl ammonium hydroxide, dioctadecyl dimethyl ammonium hydroxide, beef tallow trimethyl ammonium hydroxide, coconut oil trimethyl ammonium hydroxide, or similar cationic surface-active agent; polyoxyalkylene alkyl ether, polyoxyalkylene alkyl phenol, polyoxyalkylene alkyl ester, polyoxyalkylene sorbitol ester, polyethylene glycol, polypropylene glycol, ethylene oxide adduct of diethylene glycol trimethyl nonanol, and polyester-type nonionic surface-active agents, as well as mixtures. Furthermore, the solvents and dispersions can be combined with iron oxide suitable for use with cosmetic products, or similar pigment, as well as zinc oxide, titanium oxide, silicon oxide, mica, talc or similar powered inorganic oxides. It is preferred that in the dispersion, an average diameter of particles of the vinyl-type polymer be within a range of 0.001 to 100 $\mu$m, preferably between 0.01 and 50 $\mu$m. This is because beyond the recommended range, a cosmetic product mixed with the emulsion will not have a sufficiently good feel to the skin or to the touch, as well as sufficient rubbing properties and pleasant sensation.

It is preferred that the vinyl-type polymer contained in the dispersion or solution have a concentration within a range of 0.1 to 95 wt. %, preferably between 5 and 85 wt. %. However, for ease of handling and compounding, the range should preferably be between 10 and 75 wt. %.

Since the cosmetic raw material of the present invention possesses excellent compounding stability with regard to cosmetic products, pleasant sensation of use, and since it imparts protective properties to the surface, it is suitable for use as a raw material for the preparation of cosmetic products. When this cosmetic raw material is used especially in skin-care products, it does not produce any unpleasant sensations, it demonstrates water repellent properties, it possesses excellent gas and moisture permeability, it is not sticky, and it imparts a refreshing feeling. Furthermore, when the cosmetic raw material is used in conjunction with hair cosmetics, it imparts water repellent properties and hair-setting properties to hair. Thus, the raw material is suitable for use with both skin-care cosmetics and hair-care cosmetics.

The cosmetic products of the present invention are composed of the cosmetic raw material in combination with another cosmetic raw material. In the context of the present invention, the term "cosmetic product" that contains the cosmetic raw material of the present invention includes all kinds of cosmetics. Reference to "cosmetic products which contain the cosmetic raw material" of the invention is not limited to specific types of cosmetic products or cosmetic raw materials. For example, the cosmetic products which relate to skin-care may be soap, body shampoo, facial cleanser, or similar cleaning cosmetic, cosmetic water, cream, milky cream cleanser, packs, or similar basic cosmetics, face powder, foundation or similar base make-up, lipstick, rouge, eye shadow, eyeliner, mascara, or similar eye make-up, nail polish or similar manicure related product, hair removal cream, shaving lotion, antiperspirant, lotion with sun protection, or other specific cosmetics, perfume, cologne, or similar aromatic cosmetics. Examples of hair cosmetics are: shampoo, hair rinse, hair treatments, permanent wave agents, hair styling material, hair growing agents, hair nutrients, and hair dyes, etc. Furthermore, cosmetic products include toothpaste and substances for the bath.

The cosmetics may be water-based solutions, oil-based solutions, creams, foams, semi-solids, or powders. In addition, they may be in spray form.

The cosmetic products of the invention consist of the cosmetic raw materials listed above in combination with other raw materials. Such other raw materials may be avocado oil, almond oil, olive oil, cacao oil, beef tallow, gum oil, wheat germ oil, sunflower oil, turtle oil, camellia oil, castor oil, grape seed oil, macadamia nut oil, mink oil, egg yolk oil, vegetable wax, coconut oil, rosehip oil, or similar fats or oils; carnauba wax, candelilla wax, whale wax, jojoba oil wax, montan wax, bee wax, lanolin wax, or similar waxes; liquid paraffin, Vaseline, paraffin, ceresin wax, microcrystalline wax, squalane, or similar hydrocarbons; lauric acid, myristic acid, palmitic acid, stearic acid, oleic acid, behenic acid, undecylic acid, oxystearic acid, linoleic acid, linolenic acid, synthetic fatty acids, or similar higher aliphatic acids; ethyl alcohol, isopropyl alcohol, lauryl alcohol, cetyl alcohol, cetostearyl alcohol, stearyl alcohol, oleyl alcohol, behenyl alcohol, lanolyl alcohol, hydrogenated lanolyl alcohol, behenyl decanol, 2-octyl dodecanol, isostearyl alcohol, or similar alcohols; cholesterol, dihydrocholesterol, phytosterol, or similar sterols; linoleic acid ether, isopropyl myristate, linoleic fatty acid isopropyl ester, hexyl laurate, myristyl myristate, cetyl myristate, 2-octyl dodecyl myristate, decyl oleate, 2-octyldodecyl oleate, hexyldecyl dimethyl octanoate, hexyldecyl 2-ethylhexanoate, cetyl palmitate, glyceryl trimyristate, caprylic/capric acid triglyceride, propylene glycol dioleate, glyceryl tri-isostearate, glyceryl trioctanoate, cetyl lactate, myristyl lactate, di-isostearyl maleate, or similar fatty acid esters; glycerine, propylene glycol, 1,3-butylene glycol, polyethylene glycol, sodium pyrrolidone carboxylate, sodium lactate, sorbitol, sodium hyaluronate, or similar moisture retaining agents; higher aliphatic acid soaps, salts of higher alcohol sulfuric acid esters, salts of N-acyl glutamic acid, surface-active agents such as salts of phosphoric acid esters, or similar anionic surface-active agents, cationic surface-active agents, betaine type, amino acid type, imidazoline type, lecithin, or similar type amphoteric surface agents, polyhydric alcohol ester type, ethylene oxide condensation type, or similar nonionic surface-active agents; dye materials such as iron oxide or similar colored facial cosmetics, zinc oxide, titanium oxide, zirconium oxide, or similar white facial cosmetics, mica, talc, cerite, or similar dye material; dimethylpolysiloxane, methylphenylpolysiloxane, octamethyltetracyclosiloxane, decamethylcylopentasiloxane, polyether-modified silicone oil, amino-modified silicone oil, trimethyl silicic acid, or similar silicone type materials; purified water; carrageenan, alginic acid, alginic acid salt, arabic gum, tragacanth gum, pectin, agar-agar, casein, starch, xanthan gum, polyvinyl alcohol, polyvinyl pyrrolidone, poly (metha) acrylic acid or its salts, poly (metha) acrylic acid ester or its derivatives, polyethylene glycol, acetic acid vinyl type resin, or similar macromolecules. The other cosmetic material may also comprise thickeners, gelating agents, anti-aging agents, static charge depressors, face moisturizers, dispersing agents, anti-decolorization agents, anti-precipitation agent, anti-sag agent, ultraviolet absorbers, antiseptics, anti-inflammatory agents, agents to control perspiration, anti-corrosion agents, fragrances, antioxidants, pH adjusting agents, spray agents, and make-up components.

Solid silicone particles can be added to the cosmetic products of the present invention. These solid silicone particles may be in resinous or rubber-like form. The resinous solid silicone particles impart a clean and refreshing feeling to hair and skin, whereas the rubber-like particles impart a feeling of softness to the skin. Aqueous suspensions of the solid silicone rubber particles are advantageous in ease of compounding. It is preferred that such particles be used in an amount of 0.1 to 99 parts by weight of the cosmetic product, preferably within a range of 0.2 to 85 wt. %. Resinous solid silicone particles can be produced by hydrolysis and condensation of hydrolyzable silanes or products of partial hydrolysis. Rubber-like solid silicone particles can be produced by cross-linking a cross-linkable silicone rubber composition and then grinding the cross-linked product. In another method, a cross-linkable silicone rubber composition is subjected to cross-linking after dispersing it in water, or other medium, and then the medium is removed. A water-based suspension of rubber-like solid silicone particles can be produced by dispersing rubber-like solid silicone particles in water with the use of a surface-active agent, and by cross-linking the particles after dispersing them in water.

In the preparation of cosmetic products of the present invention, the cosmetic raw materials of the present invention can be homogeneously mixed with other cosmetic raw materials. Various mixers and kneaders used for the preparation of conventional cosmetics can be used such as a homomixer, paddle mixer, Henschel mixer, homodisperser, colloid mixer, propeller stirrer, homogenizer, in-line continuous-action emulsifier, ultrasonic emulsifier or, vacuum-type kneader.

EXAMPLES

The invention will be further described by way of practical examples. In these examples, all values of viscosity correspond to 25° C. Properties of the vinyl-type polymers which were used as cosmetic raw materials and which have carbosiloxane dendrimer structures, as well as the properties of cosmetic products were evaluated by the methods described below.
Properties of the Vinyl-Type Polymers having Carbosiloxane Dendrimer Structures
1. Molecular Weight Molecular weight was measured by means of gel permeation chromatography (GPC). Results of the measurements were represented as a number-average molecular weight referenced to polystyrene.
2. Water-Repellant Properties A 20 wt % toluene solution of the polymer was spread over a glass plate and the solvent was removed by drying in air and in an oven at 100° C. A drop of water was then applied onto the surface, and a contact angle of the water drop with the surface was measured. Measurements were conducted with the use of an automatic contact angle measurement instrument, a product of Kyowa Kaimen Chemical Co., Ltd.
3. Oxygen Permeability Oxygen permeability was measured under conditions of 23° C., humidity 0%, and 5% oxygen concentration by means of an oxygen permeability test procedure specified by JISK-7126 (Japanese Industrial Standard). Measurements were carried out by means of an oxygen permeation tester which was a product of Modem Control Company, Model 10/50. A sample of the polymer was in the form of a specimen with a coating film surface area of 50 $cm^2$. Measured value P of permeability was represented as $10^{10}$ of the oxygen permeation coefficient in the units of $cm^3 \cdot cm/(cm^2 \cdot sec \cdot mmHg)$.
4. Glass Transition Point (Tg)

This characteristic was measured by means of Differential Scanning Calorimetry (DSC).
Methods of Evaluating Cosmetic Products
1. Adhesiveness Each member of a panel of 10 people rubbed a cosmetic product into their wrist using their fingers, and then bent their wrists back and forth. After repeating the wrist-bending movement 50 times, the residual amount of the cosmetic product that adhered to the wrist was evaluated by touch. The symbol ○ was used to designate that 8 to 10 panel members felt that the cosmetic product had adhered to the wrist; symbol Δ was used to designate that 4 to 7 panel members felt that the cosmetic product had adhered to the wrist; and symbol X was used to designate that less than 3 panel members felt that the cosmetic product had adhered to the wrist.

2. Speed of Drying

Each member of a panel of 10 people rubbed a cosmetic product over the back of the hand with their fingers, and then a relative comparison of the speed of drying was conducted for the cosmetic products. The symbol ○ was used to designate that 8 to 10 panel members felt that the cosmetic product dried fast; the symbol Δ was used to designate that 4 to 7 panel members felt that the cosmetic product dried fast; and the symbol X was used to designate that less than 3 panel members felt that the cosmetic product dried fast.

3. Water-Repellant Properties

Each member of a panel of 10 people rubbed a cosmetic product into the back of their wrists using their fingers, and then the back of the hand was washed with a liquid soap and wiped with a towel. A water drop was then applied, and water-repellant properties were judged by observing the spreading of the drop. The symbol ○ was used to designate that 8 to 10 panel members felt that that the drop had spread out; the symbol Δ was used to designate that 4 to 7 panel members felt that the drop had spread out; and the symbol X was used to designate that less than 3 panel members felt that the drop had spread out.

4. Hair-Setting Holding Properties

After the hair was curled, it was treated with a spray, and a panel of 10 people evaluated the curl-holding properties after holding a wet towel on the hair for 5 min. The symbol ○ was used to designate that 8 to 10 panel members felt that the curls were stable; the symbol Δ was used to designate that 4 to 7 panel members felt that the curls were stable; and the symbol X was used to designate that less than 3 panel members felt that the curls were stable.

Practical Example 1

A flask filled with nitrogen and equipped with a stirrer was loaded with 30 parts by weight of a carbosiloxane dendrimer of the formula given below and with 400 parts by weight of a cyclic dimethylpolysiloxane (pentamer). After the components had been mixed, 1.0 part by weight of a radical polymerization initiator (V-601, a product of Wako Pure Chemical Industries Co., Ltd.) was added and mixed. The mixture was stirred with heating at 80° and then held for 6 hours. The obtained polymer dispersion turned white. This polymer dispersion produced an odor of unreacted methyl methacrylate. The methyl methacrylate odor was eliminated after the low-molecular-weight substances and the cyclic dimethyl silicone (pentamer), having a combined contents of about 200 parts by weight, were removed from the polymer dispersion by treating it for 30 min at a temperature below 140° C. under a reduced pressure of 10 mm Hg. In terms of non-volatile components, the yield of the polymer was 95 wt. %. A cyclic dimethyl silicone pentamer was added, and a dispersion of a vinyl-type polymer having a carbosiloxane dendrimer structure with 20 wt. % non-volatile components was obtained {Cosmetic Raw Material (A)}. Properties of Cosmetic Raw Material (A) are shown in Table 1.

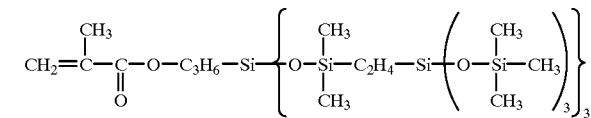

Practical Example 2

A flask filled with nitrogen and equipped with a stirrer was loaded with the following components: 30 parts by weight of the carbosiloxane dendrimer used in Practical Example 1; 45 parts by weight of methyl methacrylate; 25 parts by weight of n-butyl acrylate; and 200 parts by weight of toluene. After the components had been mixed, 1.0 part by weight of a radical polymerization initiator (V-601, a product of Wako Pure Chemical Industries Co., Ltd.) was added and mixed. The mixture was stirred with heating at 80° and then held for 5 hours. The obtained polymer dispersion was colorless. After the low-molecular-weight substances and the toluene, having a combined content of about 150 parts by weight, were removed by treating the polymer for 30 min at a temperature of 100° C. under a reduced pressure of 10 mm Hg, the product was subjected to re-precipitation with methanol and was purified and dried. The obtained polymer was ground to a fine powder in a ball mill. In terms of weight, the yield of the polymer was 92 wt. %. This polymer was diluted with a cyclic dimethylsilicone (pentamer), whereby a solution having 20 wt. % concentration of a vinyl-type polymer with a carbosiloxane dendrimer structure was produced {Cosmetic Raw Material (B)}. Properties of Cosmetic Raw Material (B) are shown in Table 1.

Practical Example 3

A flask filled with nitrogen and equipped with a stirrer was loaded with the following components: 15 parts by weight of the carbosiloxane dendrimer used in Practical Example 1; 42 parts by weight of n-butyl methacrylate; 20 parts by weight of methacrylic acid; and 400 parts by weight of ethanol. After the components had been mixed, 1.0 part by weight of a radical polymerization initiator (V-601, a product of Wako Pure Chemical Industries Co., Ltd.) was added and mixed. The mixture was stirred with heating at 80° and then retained for 5 hours. The obtained copolymer solution was heated, and after removal of the ethanol, the product was treated for 10 min at 1 50° C. and 10 mm Hg, whereby the odor was eliminated. In terms of the theoretical contents of non-volatile components, the yield of the polymer was 96 wt. %. After combining and mixing with 400 parts by weight of the pentamer, 23 parts by weight of triethanolamine were added, whereby a vinyl-type polymer solution having 20 wt. % concentration of non-volatile components was produced {Cosmetic Raw Material (C)}. Properties of Cosmetic Raw Material (C) are shown in Table 1.

Practical Example 4

A flask filled with nitrogen and equipped with a stirrer was loaded with the following components: 15 parts by weight of the carbosiloxane dendrimer used in Practical Example 1; 42 parts by weight of n-butyl methacrylate; 20 parts by weight of methacrylic acid; and 200 parts by weight of ethanol. After the components had been mixed, 1.0 part by weight of a radical polymerization initiator (V-601, a product of Wako Pure Chemical Industries Co., Ltd.) was added and mixed. The mixture was stirred with heating at 80° and then retained for 5 hours. The obtained copolymer solution was combined with 23 parts by weight of triethanolamine added at room temperature. The solution was subjected to re-precipitation with hexane, and after sufficient purification and drying, the obtained polymer was ground to a fine powder in a ball mill. In terms of weight, the yield of the polymer was 92 wt. %.

This polymer was diluted with ethanol, whereby a 20 wt. % solution of a vinyl-type polymer having a carbosiloxane dendrimer structure was produced {Cosmetic Raw Material (D)}. Properties of Cosmetic Raw Material (D) are shown in Table 1.

Comparative Example 1

A 20 wt. % solution of a vinyl-type polymer {Cosmetic Raw Material (E)} was prepared by the same method as in Practical Example 1, with the exception that 30 parts by weight of the organopolysiloxane of the formula given below were used instead of 30 parts by weight of the carbosiloxane dendrimer used in Practical Example 1. Properties of Cosmetic Raw Material (E) are shown in Table 1.

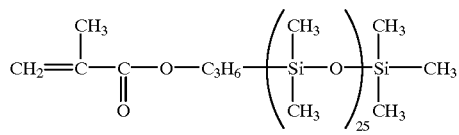

Comparative Example 2

A solution having a 20 wt. % concentration of a vinyl-type polymer {Cosmetic Raw Material (F)} was prepared by the same method as in Practical Example 1, with the exception that 30 parts by weight of an organopolysiloxane of the formula given below were used instead of 30 parts by weight of the carbosiloxane dendrimer used in Practical Example 1. Properties of Cosmetic Raw Material (F) are shown in Table 1.

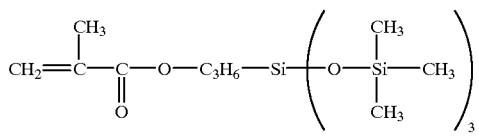

Comparative Example 3

A vinyl-type polymer was prepared by the same method as in Practical Example 1, with the exception that 30 parts by weight of methyl methacrylate were used instead of 30 parts by weight of the carbosiloxane dendrimer used in Practical Example 1. It was impossible, however, to dissolve the obtained polymer in the cyclic dimethyl silicone (pentamer).

TABLE 1

| | Practical Example 1 | Practical Example 2 | Practical Example 3 | Practical Example 4 | Comparative Example 1 | Comparative Example 2 |
|---|---|---|---|---|---|---|
| Cosmetic Raw Material | (A) | (B) | (C) | (D) | (E) | (F) |
| Molecular Weight | 23000 | 15300 | 24500 | 25800 | 23700 | 24300 |
| Water-Repellant Properties (° C.) | 107 | 107 | 107 | 107 | 101 | 105 |
| Oxygen Permeation (P) | 5.8 | 4.9 | 3.4 | 3.7 | 0.6 | 1.5 |
| Tg (° C.) | 20 | 20 | 30 | 31 | 23 | 25 |

Practical Example 5

Lipstick

A mixture was prepared from 55 parts by weight of Cosmetic Raw Material (A), 20 parts by weight of a dimethyl polysiloxane having trimethylsiloxy groups on both molecular terminals and a viscosity of 2 mPa·s, 5 parts by weight of liquid lanolin, 3.8 parts by weight of castor oil, and 8 parts by weight of glyceryl tri-isostearate. After mixing the components with heating at 85° C., the following components were added: 0.1 parts by weight of an anti-oxidant, 0.1 parts by weight of a fragrant substance, 2.0 parts by weight of a silicone treated titanium oxide, 2 parts by weight of Red 201 No.2 pigment, 1 part by weight of Red 202 No. 2 pigment, and 3 parts by weight of Yellow No. 4 Aluminum Lake pigment. The mixture was uniformly stirred, deaerated, loaded into a container, and prepared in the form of an oily lipstick. The lipstick properties were evaluated. The results of the evaluation are shown in Table 2.

Comparative Example 4

Lipstick

A lipstick was prepared by the same method as in Practical Example 5, with the exception that Cosmetic Raw Material (E) was used instead of Cosmetic Raw Material (A). The lipstick properties were evaluated. The results of the evaluation are shown in Table 2.

Comparative Example 5

Lipstick

A lipstick was prepared by the same method as in Practical Example 5, with the exception that Cosmetic Raw Material (F) was used instead of Cosmetic Raw Material (A). The lipstick properties were evaluated. The results of the evaluation are shown in Table 2.

TABLE 2

| | Practical Example 5 | Comparative Example 4 | Comparative Example 5 |
|---|---|---|---|
| Ease of rubbing | ○ | ○ | Δ |
| Non-tackiness | ○ | Δ | ○ |
| Moisture | ○ | ○ | X |
| Resistance to Color Transfer | ○ | X | ○ |
| Adhesiveness | ○ | Δ | X |
| Speed of Drying | ○ | X | X |

Practical Example 6

Mascara 62 parts by weight of Cosmetic Raw Material (B), 15 parts by weight of dextrin fatty acid ester, and 4.5 parts by weight of a low-boiling-point isoparaffin IP Solvent, a product of Idemitsu Petrochemical Co., Ltd. were heated, melted, and mixed. The product was then combined and mixed with 2 parts by weight of a hydrophobized silicic acid anhydride, 1.5 parts by weight of an organic bentonite, 7 parts by weight of black iron oxide powder, and 10 parts by weight of mica. The mixture was loaded into a container and prepared in the form of a mascara. The properties of the mascara were evaluated. The results of the evaluation are shown in Table 3.

Comparative Example 6

Mascara

A mascara was prepared by the same method as in Practical Example 6 with the exception that 62 parts by weight of a 20 wt. % solution of a trimethylsiloxysilicic acid ($Me_3SiO_{1/2}$:$SiO_2$ 1.5:1.0) were used instead of 62 parts by weight of Cosmetic Raw Material (B). The properties of the mascara were evaluated. The results of the evaluation are shown in Table 3.

Comparative Example 7

Mascara

A mascara was prepared by the same method as in Practical Example 6, with the exception that Cosmetic Raw Material (E) was used instead of Cosmetic Raw Material (B). The mascara properties were evaluated. The results of the evaluation are shown in Table 3.

TABLE 3

|  | Practical Example 6 | Comparative Example 6 | Comparative Example 7 |
| --- | --- | --- | --- |
| Ease of applying | ○ | X | ○ |
| Property to Curl | ○ | Δ | Δ |
| Adhesiveness | ○ | X | Δ |
| Speed of Drying | ○ | X | X |
| Water-Repellant Properties | ○ | Δ | ○ |

Practical Example 7

Nail Polish for Manicure

A uniform mixture was prepared from 40 parts by weight of Cosmetic Raw Material (C), 15 parts by weight of nitrocellulose, 5 parts by weight of sucrose acetate isobutylate, 5 parts by weight of acetyl tributyl citrate, 2 parts by weight of camphor, 5 parts by weight of ethyl acetate, 10 parts by weight of butyl acetate, 17 parts by weight of toluene, 1 part by weight of an organic bentonite, and 1 part by weight of a pigment. The mixture was loaded into a container, and a nail polish for manicure was prepared. Properties of the obtained product were evaluated. The results of the evaluation are shown in Table 4.

Comparative Example 8

Nail Polish for Manicure

A nail polish for manicure was prepared by the same method as in Practical Example 7 with the exception that Cosmetic Raw Material (E) was used instead of Cosmetic Raw Material (C). The nail polish was evaluated. The results of the evaluation are shown in Table 4.

Comparative Example 9

Nail Polish for Manicure

A nail polish for manicure was prepared by the same method as in Practical Example 7 with the exception that Cosmetic Raw Material (F) was used instead of Cosmetic Raw Material (C). The nail polish was evaluated. The results of the evaluation are shown in Table 4.

TABLE 4

|  | Practical Example 7 | Comparative Example 3 | Comparative Example 9 |
| --- | --- | --- | --- |
| Ease of rubbing | ○ | Δ | Δ |
| Smoothness of the film | ○ | X | ○ |
| Adhesiveness | ○ | Δ | X |
| Speed of Drying | Δ | X | Δ |
| Water-Repellant Properties | ○ | ○ | Δ |

Practical Example 8

Skin Cream Cosmetic Product

A Henschel mixer was loaded with 15 parts by weight of Cosmetic Raw Material (A), 2 parts by weight of silicone-treated titanium oxide powder, 10 parts by weight of octyl p-methoxy cinnamate, 12 parts by weight of a 20 mP·s viscosity dimethylpolysiloxane having trimethylsiloxy groups on both molecular terminals, 3 parts by weight of polyoxyethylene (40 mole adduct) solid castor oil, 60 parts by weight of squalane, 5 parts by weight of glycerin, 3 parts by weight of beeswax, an appropriate amount of antiseptic agent, an appropriate amount of fragrance, and an appropriate amount of purified water. The components were stirred for 10 min at 1500 rpm whereby a skin cream cosmetic product was prepared. Properties of the product were evaluated. The results are shown in Table 5.

Practical Example 10

Skin Cream Cosmetic Product

A skin cream cosmetic product was prepared by the same method as in Practical Example 8 with the exception that 15 parts by weight of a 20 wt. % solution of a trimethylsiloxy silicic acid ($Me_3SiO_{1/2}$:$SiO_2$=1.5:1.0) were used instead of 15 parts by weight of Cosmetic Raw Material (A). Results of the evaluation of the properties are shown in Table 5.

Comparative Example 11

Skin Cream Cosmetic Product

A skin cream cosmetic product was prepared by the same method as in Practical Example 8 with the exception that 15 parts by weight of Cosmetic Raw Material (F) were used instead of Cosmetic Raw Material (A). Results of the evaluation of the properties are shown in Table 5.

TABLE 5

|  | Practical Example 8 | Comparative Example 10 | Comparative Example 11 |
| --- | --- | --- | --- |
| Ease of rubbing | ○ | X | Δ |
| Feel by touch | ○ | Δ | ○ |
| Adhesiveness | ○ | X | Δ |
| Water-Repellant Properties | ○ | Δ | Δ |

Practical Example 9

Shampoo

A mixture was prepared from 20 parts by weight of disodium monolauryl sulfosuccinate,-2 parts by weight of lauroyl diethanolamide, 5 parts by weight of Cosmetic Raw Material (C), 0.2 parts by weight of fragrance, 0.1 parts by weight of an antiseptic agent; 72.5 parts by weight of purified water, and a minute quantity of pigment. The mixture was loaded into a container, and a shampoo was prepared. The shampoo was evaluated, and the results of the evaluation are shown in Table 6.

Comparative Example 12

Shampoo

A shampoo was prepared by the same method as in Practical Example 9 with the exception that 5 parts by weight of Cosmetic Raw Material (E) were used instead of Cosmetic Raw Material (C). Results of the evaluation of the properties are shown in Table 6.

Comparative Example 13

Shampoo

A shampoo was prepared by the same method as in Practical Example 9 with the exception that 5 parts by weight of Cosmetic Raw Material (F) were used instead of Cosmetic Raw Material (C). Results of evaluation of properties are shown in Table 6.

TABLE 6

|  | Practical Example 9 | Comparative Example 12 | Comparative Example 13 |
| --- | --- | --- | --- |
| Shine and luster of hair after washing | ◯ | Δ | Δ |
| Hair setting | ◯ | X | ◯ |
| Adhesiveness | ◯ | Δ | X |
| Water-Repellant Properties | ◯ | ◯ | Δ |

Practical Example 10

Hair Spray 100 parts by weight of Cosmetic Raw Material (D), 50 parts by weight of ethanol, and 35 parts by weight of liquefied petroleum gas were cooled, mixed, and used for the preparation of an aerosol-type spray. Properties of the spray were evaluated. Results of the evaluation are shown in Table 7.

Comparative Example 14

Hair Spray

A hair spray was prepared by the same method as in Practical Example 10, with the exception that Cosmetic Raw Material (E) was used instead of Cosmetic Raw Material (D). Properties of the spray were evaluated. Results of the evaluation are shown in Table 7.

Comparative Example 15

Hair Spray

A hair spray was prepared by the same method as in Practical Example 10, with the exception that Cosmetic Raw Material (F) was used instead of Cosmetic Raw Material (D). Properties of the spray were evaluated. Results of the evaluation are shown in Table 7.

TABLE 7

|  | Practical Example 10 | Comparative Example 14 | Comparative Example 15 |
| --- | --- | --- | --- |
| Shine and luster of hair after washing | ◯ | ◯ | Δ |
| Hair setting | ◯ | X | ◯ |
| Adhesiveness | ◯ | X | Δ |
| Water-Repellant Properties | ◯ | ◯ | Δ |

Since the cosmetic raw material of the invention is a solution or a dispersion prepared from a vinyl-type polymer having a carbosiloxane dendrimer in its side chain, and a liquid such as a silicone oil, an organic oil, alcohol, or water, it can impart excellent compounding stability, pleasant sense of use, and surface protection properties to cosmetic products. Thus, when a cosmetic product prepared from a cosmetic raw material of the invention is used in conjunction with skin cosmetics, it does not produce an unpleasant feeling, it has a good sensation of use, imparts good water-repellent properties to the skin surface, and possesses excellent oxygen permeability. When it is used in conjunction with hair cosmetics, it imparts water-repellent properties to hair and good hair-setting properties. Furthermore, the cosmetic products of the invention are characterized by efficiency of production when produced by the method of the invention.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A method of treating skin or hair comprising applying to skin or hair in need thereof, a cosmetic product comprising a solution or dispersion of a polymer in a liquid selected from the group consisting of silicone oils, organic oils, alcohols and water, the polymer having a carbosiloxane dendrimer in its side molecular chain comprising a polymer obtained by polymerizing:

(A) 0 to 99.9 parts by weight of a vinyl monomer; and (B) 100 to 0.1 parts by weight of a carbosiloxane dendrimer which contains an organic group of the formula:

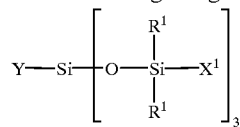

where Y is a radical-polymerizable organic group, $R^1$ is an aryl group or an alkyl group having 1 to 10 carbon atoms, and $X^1$ is a silylalkyl group which when i=1 has the formula:

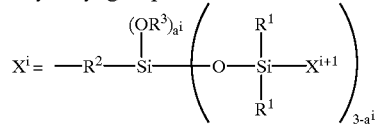

where $R^1$ is the same as defined above, $R^2$ is an alkylene group with 2 to 10 carbon atoms, $R^3$ is an alkyl group having 1 to 10 carbon atoms, $X^{i+1}$ is a hydrogen atom, an alkyl group having 1 to 10 carbon atoms, an aryl group, or said silylalkyl group; i is an integer from 1 to 10 which represents the generation of said silylalkyl group, and $a^i$ is an integer from 0 to 3; with the proviso that when i=10, $X^{i+1}$ cannot be said silylalkyl group; wherein said radical-polymerizable organic group Y contained in component (B) is selected from the group consisting of groups having the formulae:

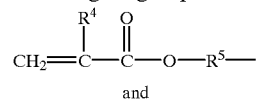

and

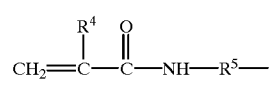

where $R^4$ is a hydrogen atom or an alkyl group, $R^5$ is an alkylene group having 1 to 10 carbon atoms; and a group having the formula:

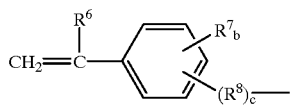

where $R^6$ is a hydrogen atom or an alkyl group, $R^7$ is an alkyl group with 1 to 10 carbon atoms, $R^8$ is an alkylene group having 1 to 10 carbon atoms, b is an integer from 0 to 4, and c is 0 or 1.

2. The method according to claim 1 in which Y, $R^1$, $R^2$, and $R^3$ are the same as defined in claim 1, $R^{12}$ is a hydrogen atom or the same as $R^1$, and the polymer has a structure selected from the group consisting of

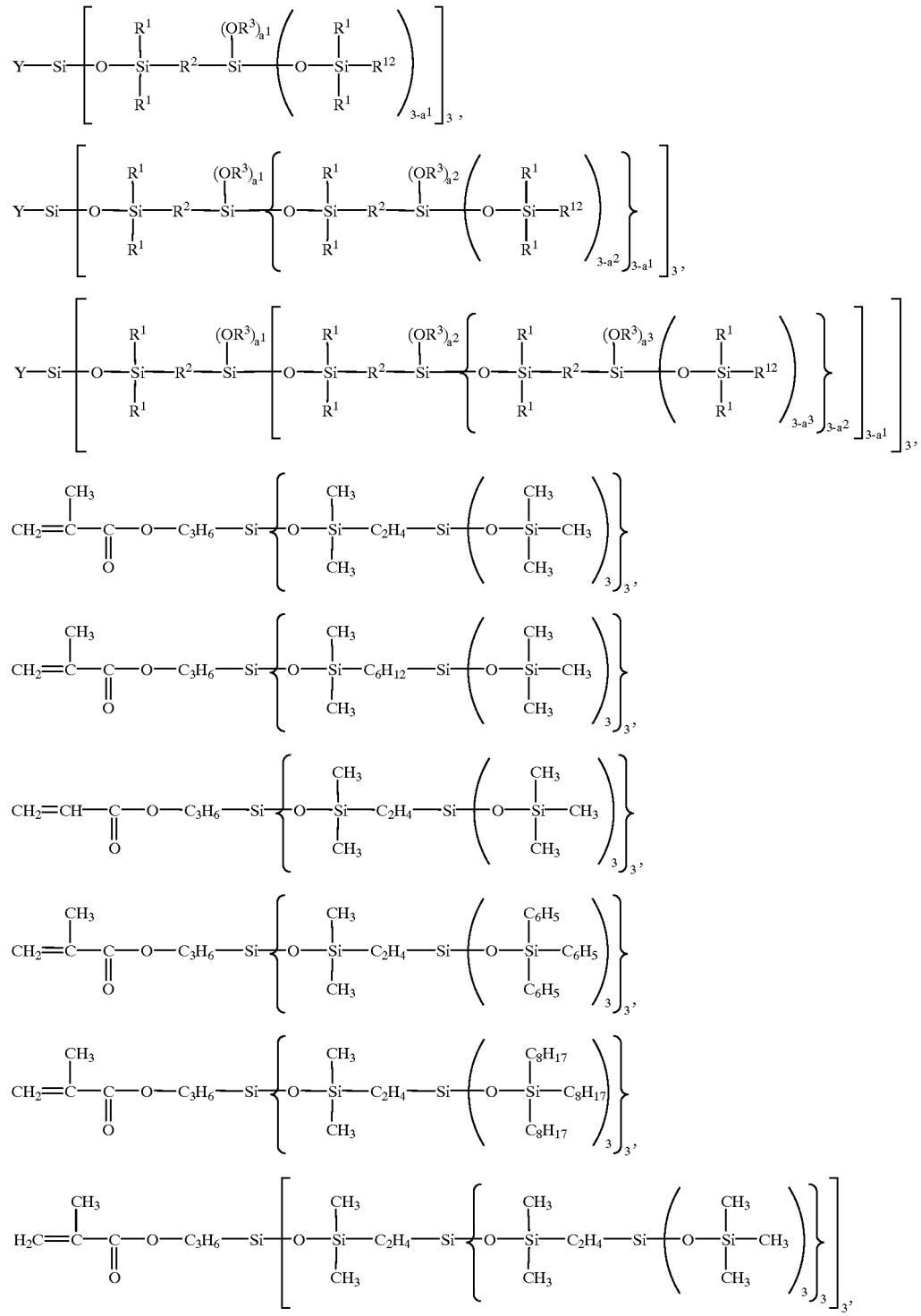

-continued
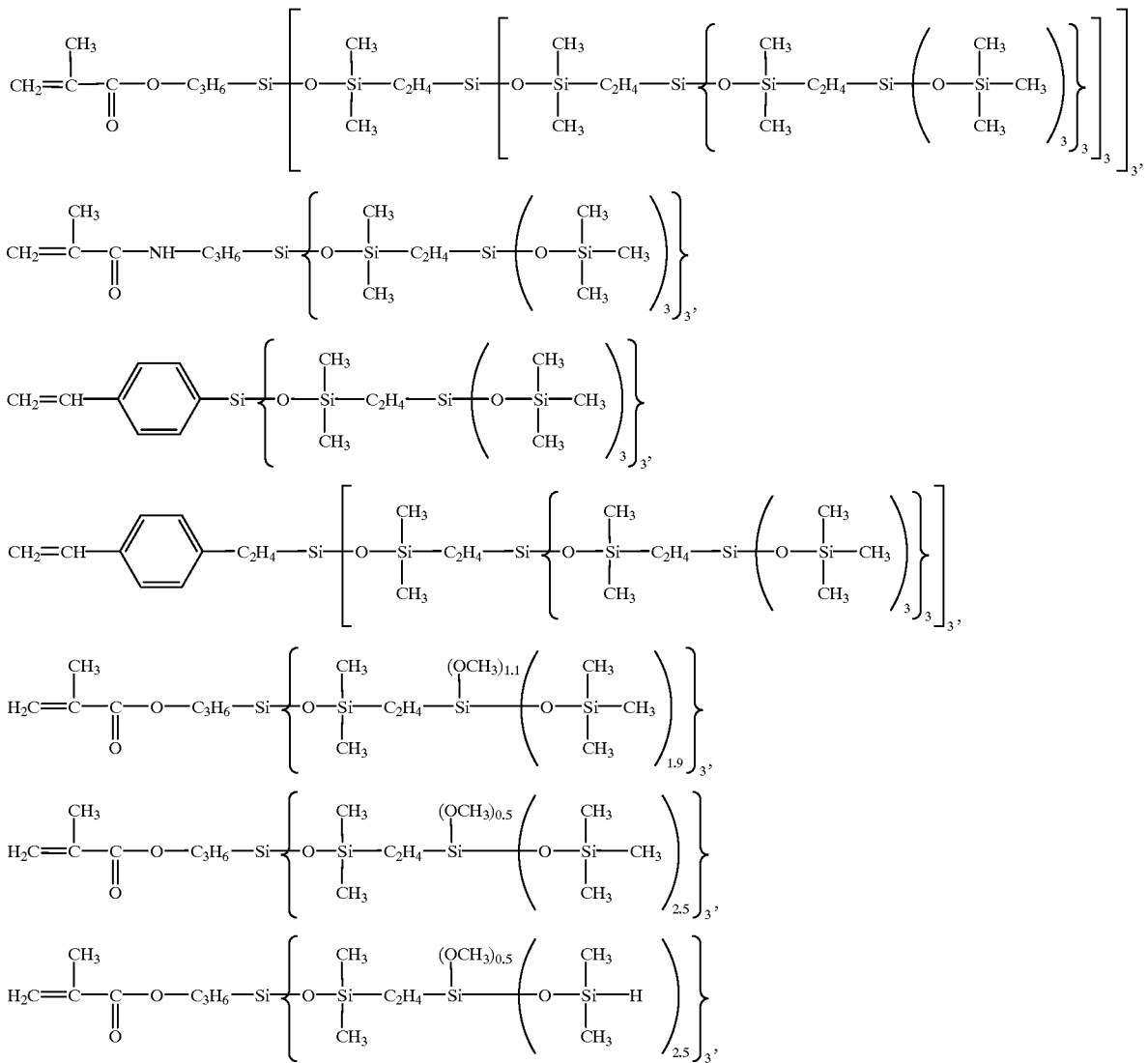
and
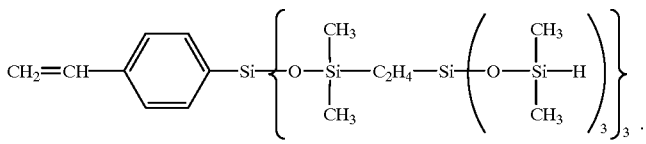
* * * * *